(12) United States Patent
Batiste

(10) Patent No.: US 7,833,186 B1
(45) Date of Patent: *Nov. 16, 2010

(54) A-V DIALYSIS GRAFT

(76) Inventor: Stanley Batiste, 708 Charbonne Pl., Las Vegas, NV (US) 89145

( * ) Notice: Subject to any disclaimer, the term of this patent is extended or adjusted under 35 U.S.C. 154(b) by 643 days.

This patent is subject to a terminal disclaimer.

(21) Appl. No.: 11/860,053

(22) Filed: Sep. 24, 2007

Related U.S. Application Data

(63) Continuation-in-part of application No. 11/457,885, filed on Jul. 27, 2006, now Pat. No. 7,566,317, which is a continuation-in-part of application No. 10/614,450, filed on Jul. 7, 2003, now Pat. No. 7,108,673.

(60) Provisional application No. 60/829,105, filed on Oct. 11, 2006, provisional application No. 60/865,718, filed on Nov. 14, 2006.

(51) Int. Cl.
*A61M 5/00* (2006.01)
*A61M 37/00* (2006.01)

(52) U.S. Cl. .......................... 604/9; 604/509

(58) Field of Classification Search ................ 604/5.04, 604/6.15, 6.1, 9, 509, 264, 507
See application file for complete search history.

(56) References Cited

U.S. PATENT DOCUMENTS

| 3,826,257 | A |   | 7/1974 | Buselmeier |
| 4,549,879 | A |   | 10/1985 | Groshong et al. |
| 4,753,640 | A |   | 6/1988 | Nichols et al. |
| 5,713,859 | A |   | 2/1998 | Finch, Jr. et al. |
| 6,056,717 | A | * | 5/2000 | Finch et al. ............. 604/93.01 |
| 6,146,414 | A |   | 11/2000 | Gelman |
| 6,461,321 | B1 |  | 10/2002 | Quinn |
| 6,585,762 | B1 |  | 7/2003 | Stanish |
| 2004/0249334 | A1 | * | 12/2004 | Cull ............................. 604/9 |

* cited by examiner

*Primary Examiner*—Leslie R Deak
(74) *Attorney, Agent, or Firm*—Sturm & Fix LLP

(57) ABSTRACT

The present invention provides an apparatus and method for optimizing flow in an A-V dialysis graft having a selectable constricted section. Electronic pressure and flow sensors in the arterial and venous ends of the graft are electronically coupled to a monitor to detect the arterial and venous environments and change the degree of stenosis to optimize flow. The stenosis or narrowing within the graft creates resistance for the purpose of decreasing the flow rate and pressure at the outflow end. The selectable restricted section may be provided by a balloon or a thin "slit" type valve with flexible leaves to provide the required resistance. The "slit" valve allows access to wires or catheters for the purpose of any type of graft maintenance.

7 Claims, 8 Drawing Sheets

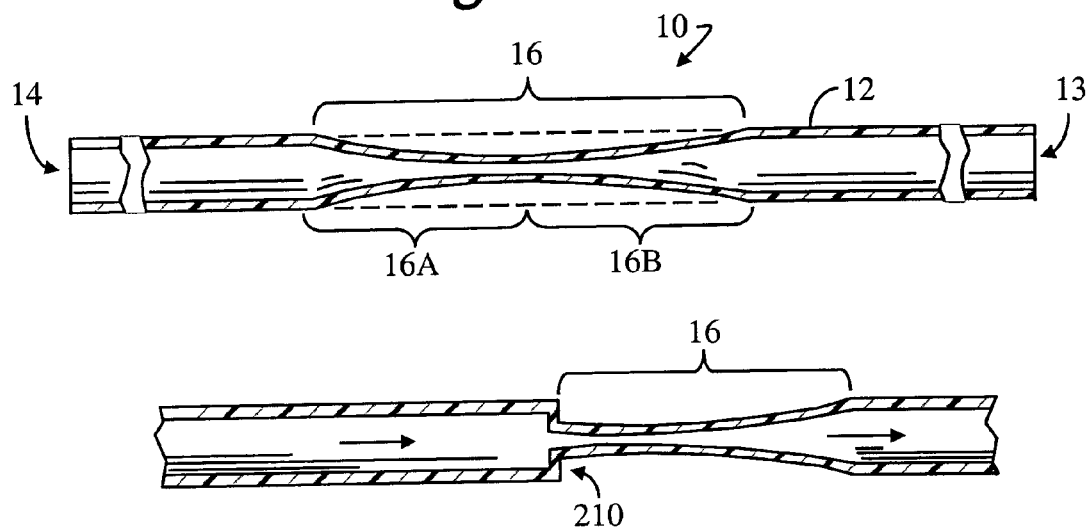
*Fig. 2A*
*Fig. 2B*
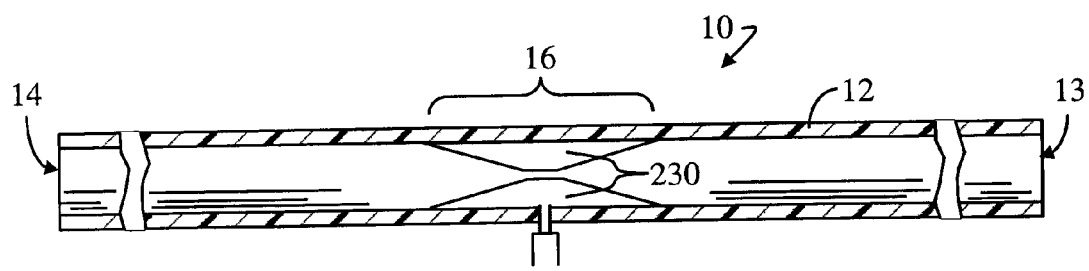
*Fig. 2C*

Fig. 9
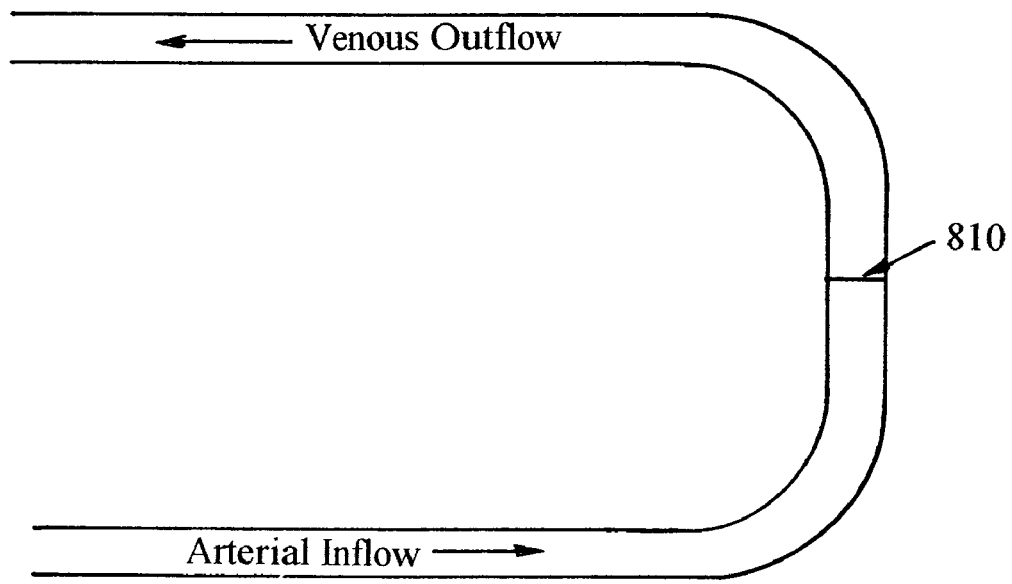
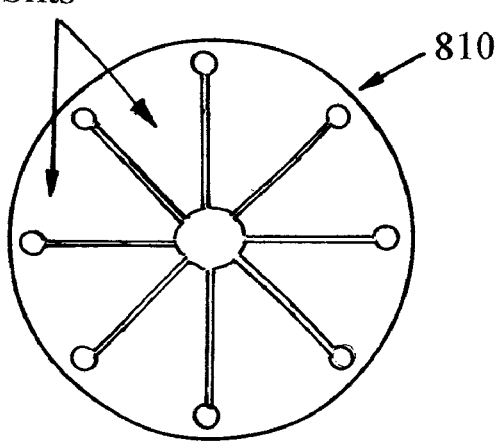
Fig. 10
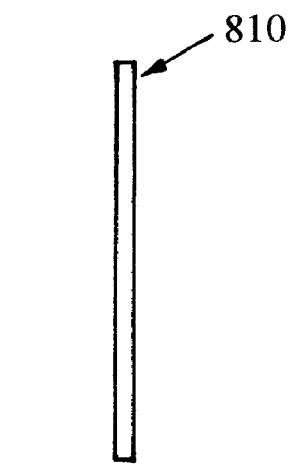
Fig. 11

Fig. 12
Slit Valve with 4 Flaps
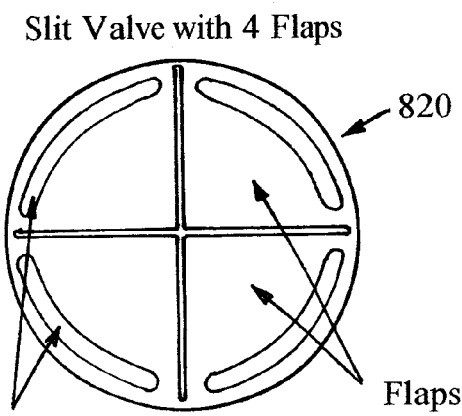
Lower Flap
Holes
Fig. 14
Single Hole opening
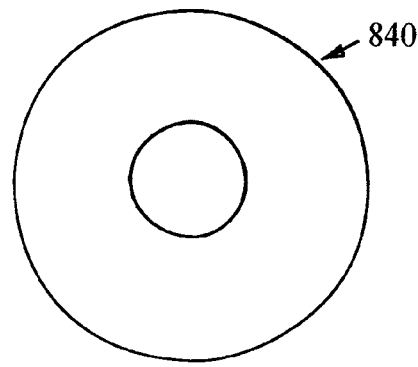
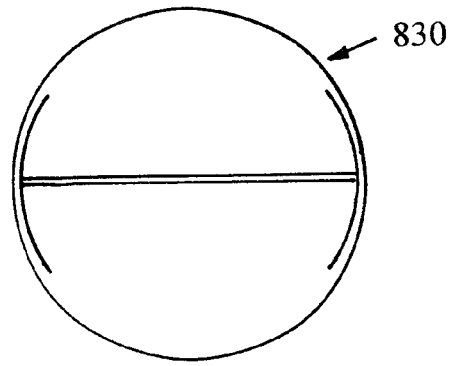
Slit Valve with 2 Flaps
Fig. 13
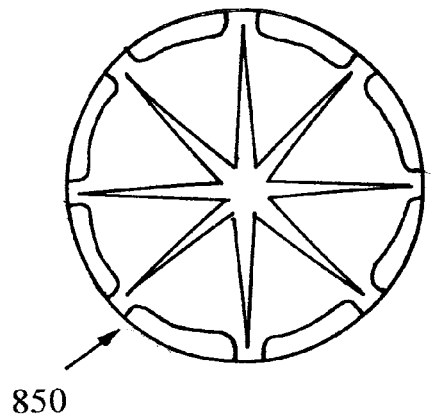
Fig. 15

A-V DIALYSIS GRAFT

CROSS REFERENCE TO RELATED APPLICATIONS

This application is a Continuation-in-Part Patent Application of U.S. Ser. No. 11/457,885, filed Jul. 27, 2006, now U.S. Pat. No. 7,566,317, issued Jul. 28, 2009, and entitled A-V DIALYSIS GRAFT; which is a Continuation-in-Part of U.S. Ser. No. 10/614,450, filed Jul. 7, 2003, entitled A-V DIALYSIS GRAFT CONSTRUCTION, now U.S. Pat. No. 7,108,673, issued Sep. 19, 2006; this application also includes disclosures contained in Provisional U.S. Application Ser. No. 60/829,105, filed Oct. 11, 2006, and entitled A-V DIALYSIS GRAFT; and Provisional U.S. Application Ser. No. 60/865,718, filed Nov. 14, 2006, and entitled A-V DIALYSIS GRAFT. Applicant claims the benefit under Title 35 United States Code §120 of all the above-identified applications, and incorporates them herein by reference in their entireties.

STATEMENT REGARDING FEDERALLY SPONSORED RESEARCH OR DEVELOPMENT

Not Applicable.

BACKGROUND OF THE INVENTION

1. Field of the Invention

The present invention relates to the field of hemo-dialysis apparatus in general and in particular to an arterial-venous graft having an intra-graft stenosis formed therein.

2. Description of Related Art

As can be seen by reference to the following U.S. Pat. Nos. 3,826,257; 4,549,879; 4,753,640; 5,713,859; 6,146,414; 6,461,321 and 6,585,762, the prior art is replete with myriad and diverse graft constructions employed for hemo-dialysis procedures.

While all of the aforementioned prior art constructions are more or less adequate for the basic purpose and function for which they have been specifically designed, they are uniformly deficient with respect to their failure to provide a simple, efficient, and practical means of forming an artificial intra-graft stenosis to provide increased blood flow resistance, and the associated pressure drop, during those periods when the higher blood flow rates required by hemo-dialysis are not present.

As virtually all physicians and health care specialists are aware, the process of hemo-dialysis requires large volumes of blood to be circulated through a filtration device. However, with prior art A-V graft designs having a uniform bore, the continued high velocity and high pressure blood flow into veins creates venous irritation and scarring leading to stenosis and eventual occlusion as well as causing increased cardiac demands.

Additionally, current dialysis shunts provide a continuous high flow which bypasses the patient's normal tissues and directs high pressure blood flow into the normally low pressure veins. This shunt creates what is called in medicine a "steal." The blood flowing through the shunt bypasses tissues and then returns to the heart. This creates undue, continued stress on the heart and can invoke a situation in which the blood flow to the hand and/or arm is compromised.

Stanish, in U.S. Pat. No. 6,585,762 discloses a graft comprising, in the streamwise direction, a diverging portion followed by a lumen of substantially constant diameter, followed by a converging portion. Because the constant diameter lumen portion of the graft has a diameter greater than the ends, the pressure drop across the Stanish graft is minimized.

Buselmeier, in U.S. Pat. No. 3,826,257 discloses a converging portion followed by a lumen having a substantially constant diameter, followed by a diverging portion. The hemo-dialysis machine access tubes are located between the converging and diverging portions, in the constant diameter lumen. This arrangement, however, defeats the purpose of the flow restrictions as almost no pressure drop exists between the two ports of the access tubes. Blood will flow through the constant diameter lumen instead of, or in opposing direction to, the dialysis machine. The flow restriction must reside between the dialysis machine's access tubes to effect the needed pressure drop.

As a consequence of the foregoing situation, there has existed a longstanding need among medical personnel for a new and improved A-V stent graft construction having a reduced diameter portion, either of fixed diameter or variable diameter, and the provision of such a construction is the stated objective of the present invention.

BRIEF SUMMARY OF THE INVENTION

Briefly stated, the present invention provides an apparatus and method for optimizing flow in an A-V dialysis graft having a selectable constricted section. Electronic pressure and flow sensors in the arterial and venous ends of the graft are electronically coupled to a monitor to detect the arterial and venous environments and change the degree of stenosis to optimize flow. The stenosis or narrowing within the graft creates resistance for the purpose of decreasing the flow rate and pressure at the outflow end. The selectable restricted section may be provided by a balloon or a thin "slit" type valve with flexible leaves to provide the required resistance. The "slit" valve allows access to wires or catheters for the purpose of any type of graft maintenance. The valve could either be manufactured in the graft of selectively attached post manufacturing.

As will be explained in greater detail, in a first preferred embodiment, the reduced diameter intermediate portion comprises a gently tapered segment having a cross sectional area that is gradually converging and gradually diverging sections, integral with the tubular member. In a second preferred embodiment, the reduced diameter portion comprises a constricted section being of selectable diameter.

In order to provide for a variable diameter flow restriction, a manufactured stenosis or a balloon can be disposed about the inner circumference of the lumen. When deflated, the balloon lies flat against the inner lumen wall. When inflated, the balloon restricts the flow by narrowing the diameter of the lumen.

In a third preferred embodiment, flow and pressure sensors, electronically coupled to a monitor, detect the arterial and venous environment and change the degree of stenosis to optimize flow.

A fourth embodiment uses a "slit" type valve to provide a selectable restricted section in the graft.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 9 is a side elevation view showing a thin slit valve disposed between the arterial and venous ends of the graft;

FIG. 10 is a front elevational view showing a slit valve;

FIG. 11 is a side elevational view thereof;

FIG. 12 is a front elevational view of an alternative slit valve;

FIG. 13 is a front elevational view of another alternate slit valve;

FIG. 14 is a front elevational view of a valve with a single hole opening; and

FIG. 15 is a front elevational view of a valve of a preferred slit valve.

DETAILED DESCRIPTION OF THE INVENTION

Figures 2, 2A, 2B, 2C:
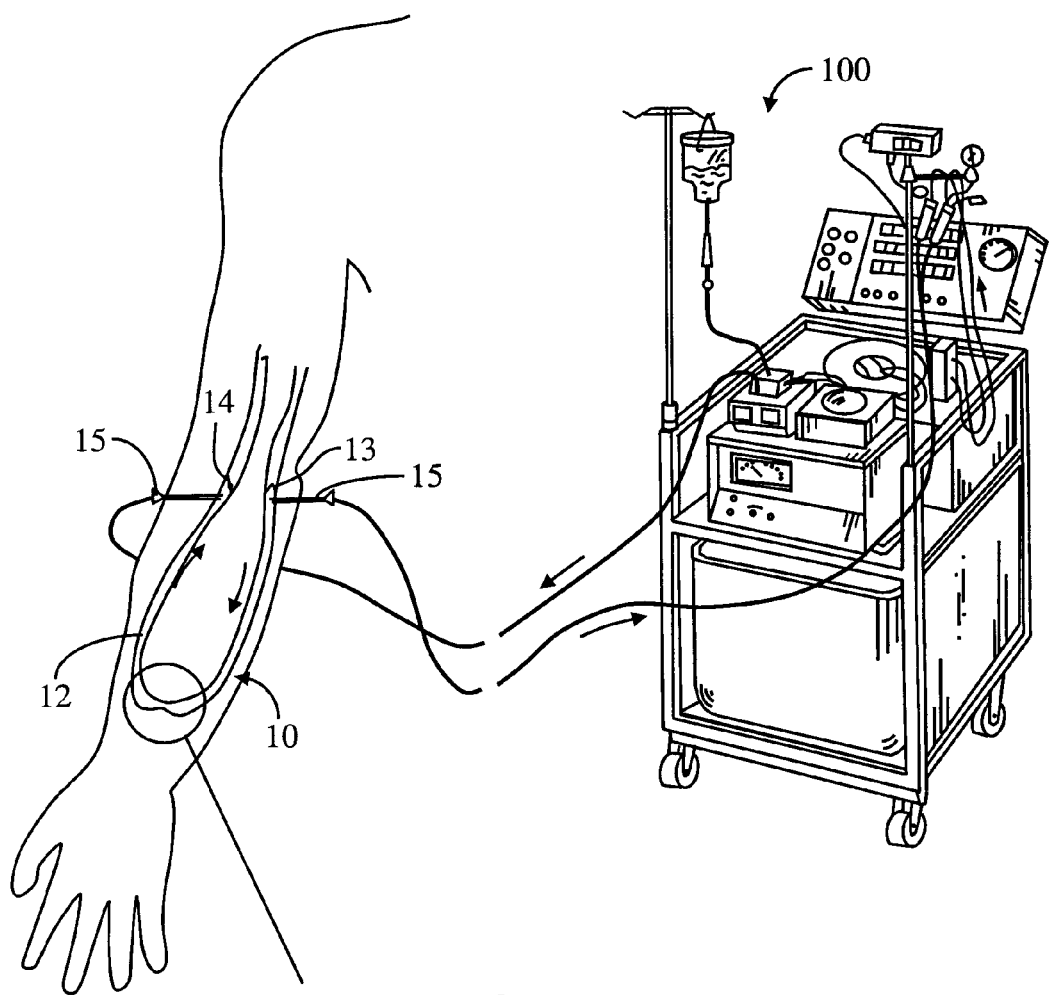
FIG. 2 is a representative perspective view of the A-V graft construction that forms the basis of the present invention.
FIG. 2A is an enlarged detail view of the gradually constricted version of the invention.
FIG. 2B is an enlarged detail view of an abruptly constricted, then gradually expanded version of the invention.
FIG. 2C is an enlarged detail view of a graft using an annular stenosis balloon to provide the stenosis between the dialysis machine access needles.

As can be seen by reference to the drawings, and in particular to FIG. 2, the improved A-V graft construction that forms the basis of the present invention is designated generally by the reference number 10. Prior to embarking on a detailed description of the improved graft construction 10, it would first be advisable to describe the conventional graft construction 11, currently used as standard equipment in virtually all modern hemo-dialysis procedures.

Figure 1:
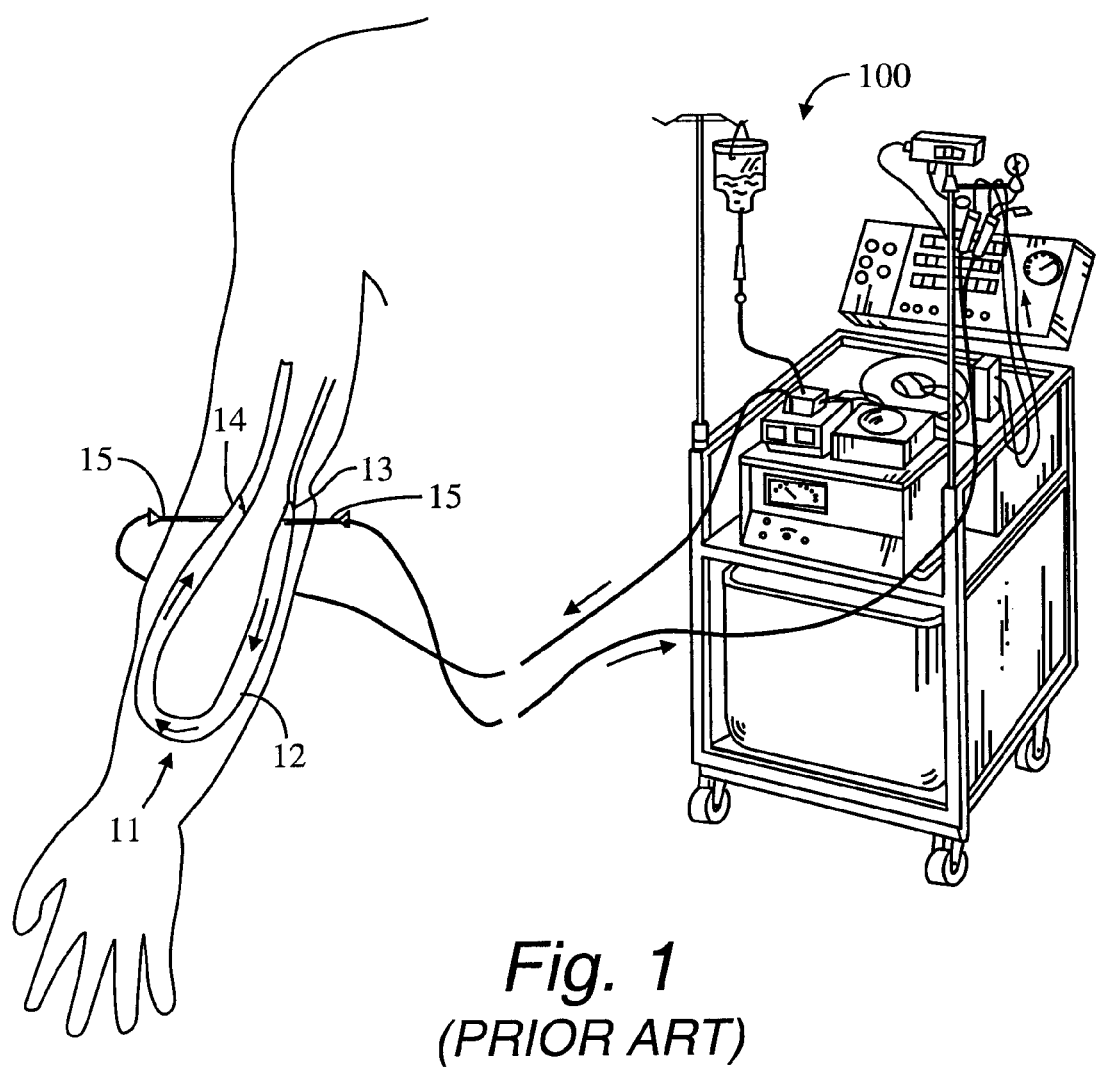
FIG. 1 is a perspective view of the prior art uniform inside diameter A-V graft construction currently employed in hemo-dialysis procedures.

As shown in FIG. 1, the prior art graft construction 11 includes an elongated length of hollow polymer tubing 12 having a uniform inside diameter extending from the inlet end 13 to the outlet end 14 wherein, the inlet end 13 defines the arterial anastomosis.

In addition, the conventional graft construction 11, as well as the improved graft construction 10, are commonly surgically placed within a patient's upper arm or forearm and connected via access needles 15 to a hemo-dialysis machine that withdraws blood from the arterial end 13 and removes impurities from the blood prior to re-introducing the cleansed blood through the venous end 14.

As was mentioned previously, the hemo-dialysis procedure, requiring abnormally high blood flow rates through the conventional uniform internal diameter graft constructions 11, and the presence of the conventional graft construction 11, allows the elevated blood flow rates to continue unsubsided during those periods when the access needles 15 are not connected to the hemo-dialysis machine 100.

As a direct consequence of these elevated blood flow rates, increased cardiac demands are imposed on the heart as blood is bypassed past the distal circulation. Further, the high flow rates results in venous irritation leading to stenosis and occlusion which typically occurs at the venous anastomosis.

As a consequence of the foregoing situation, and as shown in FIG. 2, the improved graft construction 10 of the present invention includes an elongated length of polymer tubing 12 having an inlet end 13, and an outlet end 14, and a reduced diameter intermediate portion 16 (see FIGS. 2A-2C) which forms the heart of this invention.

In the first preferred embodiment, depicted in FIG. 2A, the intermediate portion 16 includes a gradually converging segment 16A and a gradually diverging segment 16B wherein, the minimum inside diameter of the intermediate portion 16 is equal to or less than ⅔ of the generally uniform inside diameter of the remainder of the length of polymer tubing 12. The intermediate stenosis 16 necessarily resides between the hemo-dialysis machine access needles 15.

Further, as depicted in FIG. 2B, this invention also contemplates a version that includes an abruptly crimped segment 210, selectively disposed upstream or downstream of a gradually diverging or converging segment 16A, 16B.

In FIG. 2C, the second embodiment of the improved graft construction 10 is detailed. Here, the polymer tubing 12 is constructed to have a substantially constant diameter throughout. The stenosis 16 is provided by an annular balloon 230 disposed about the inner circumference of the polymer tubing 12. The annular balloon 230 provides an opportunity to vary the stenosis 16. It is to be understood that structures other than an annular balloon could be used to provide a variable stenosis.

The configuration of the annular stenosis balloon 230 may range from abrupt to smoothly tapering. As with the first embodiment of the improved graft construction 10, the annular balloon 230 stenosis is positioned between both access needles 15 of the graft as clearly seen in FIG. 5. The design intentionally maintains high pressure on the arterial end 13 and lower pressure for the incoming returning blood from the hemo-dialysis machine 100 to the patient at the venous end 14.

Figure 5:
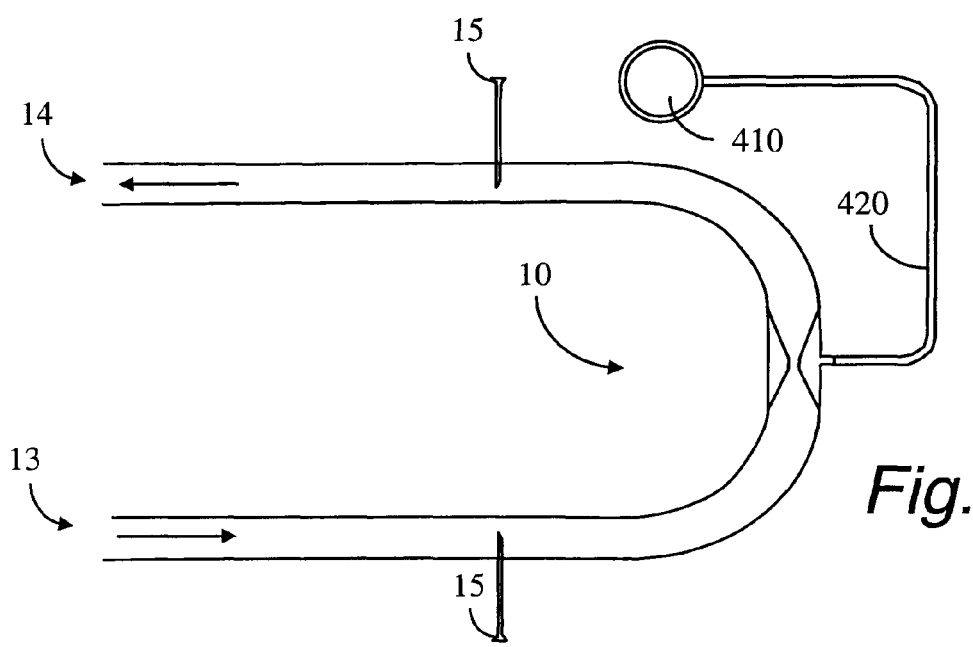
FIG. 5 is a side elevation view of the second embodiment with the annular stenosis balloon in its inflated mode.

The design of the second embodiment of the improved dialysis graft construction 10 is shown in FIGS. 2C-6C and utilizes the annular stenosis balloon 230 for adjusting and maintaining the intermediate stenosis 16. This embodiment of the improved dialysis graft construction 10 comprises four main components: the polymer tubing 12, the annular stenosis balloon 230, the injection reservoir 410, and the catheter 420 connecting the reservoir 410 to the annular stenosis balloon 230. The injection reservoir 410 and the catheter 420 are detailed in FIG. 4. The entire assembly, shown in FIG. 5, is placed surgically and remains under a patient's skin for the life of the device which is the standard of care for current, standard A-V dialysis grafts 11.

Figure 6A:
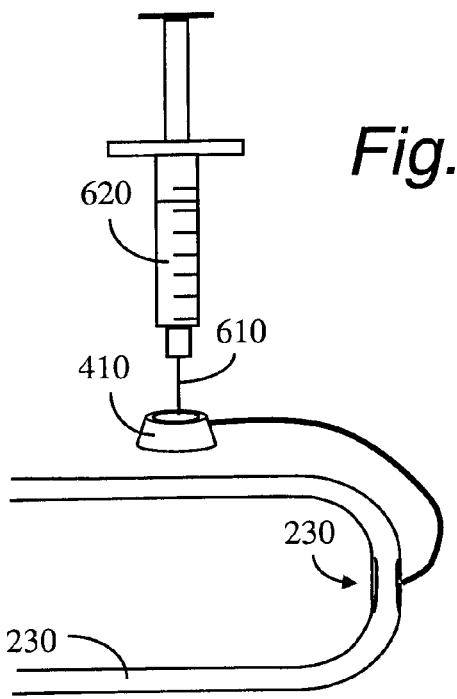
FIG. 6A is a first view of a syringe being used to inflate the balloon.
Figure 6B:
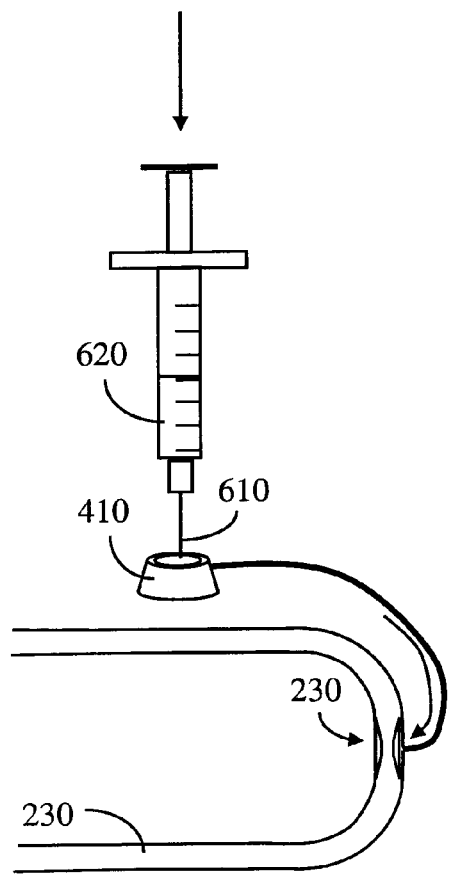
FIG. 6B is a second view of a syringe being used to inflate the balloon.
Figure 6C:
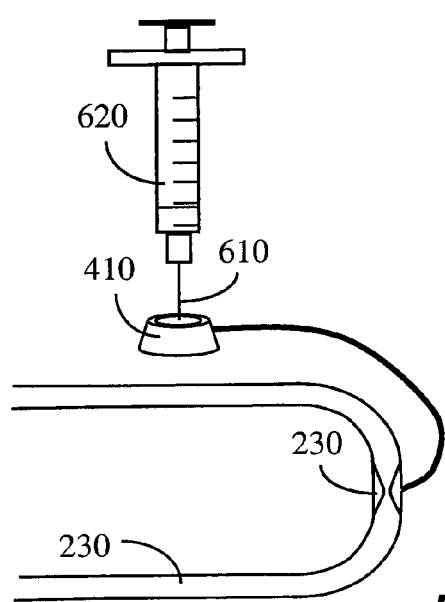
FIG. 6C is a third view of a syringe being used to inflate the balloon.

As shown in FIGS. 4 and 6A-6C, the injection reservoir 410 communicates with the stenosis balloon 230 by way of a small caliber catheter 420. The reservoir 410 comprises a puncture resistant outer wall 430 and bottom (not shown), with a puncturable, self-sealing, pressure resistant top 440 as is common with many access ports used today in the healthcare field, as those of ordinary skill know. The reservoir 410 is accessed using a needle 610 and syringe 620 through the reservoir top 440. The syringe 620 is used to inject fluid into the reservoir 410, which then travels through the small catheter 420 and under pressure inflates the annular stenosis balloon 230. FIGS. 6A-6C chronicle the inflation procedure. The amount of stenosis created is directly related to a volume of fluid injected. Once the desired stenosis is achieved, the needle 610 is removed from the reservoir top 440, and the pressure within the reservoir 410, catheter 420, and annular stenosis balloon 230 remains, thus maintaining the degree of stenosis.

Figure 3A:
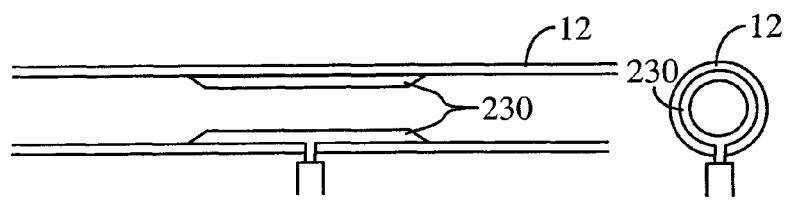
FIG. 3A is an enlarged detail view of the second embodiment of the invention, showing the annular stenosis balloon used to provide a variable diameter stenosis in a deflated mode.
Figure 3B:
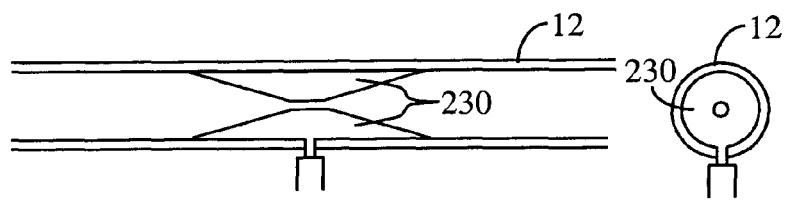
FIG. 3B is an enlarged detail view of the second embodiment of the invention, showing athe annular stenosis balloon used to provide a variable diameter stenosis in an inflated mode.
Figure 4:
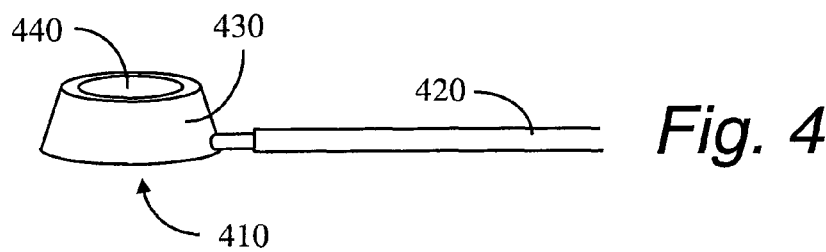
FIG. 4 is a perspective view of an injection reservoir for inflating and deflating the annular stenosis balloon.

Advantages of the adjustable annular stenosis balloon graft construction 10 are many. A primary advantage is seen when attempting to maintain patency of the graft 10. For example, if there is intimal hyperplasia (fibrous growth on the walls of the balloon 230) the stenosis can become more restrictive, possibly below an optimal range. This problem is evaluated using one or more of several known techniques. The stenosis can then be corrected to again be within the optional range by varying the inflation of the stenosis balloon 230. Additionally, if an occlusion occurs within the graft 10 for any reason, the annular stenosis balloon 230 can be deflated, as shown in FIG. 3A, thereby removing the stenosis, and the graft 10 cleared using standard medical techniques. This design feature significantly improves the ability to maintain the graft 10. Another advantage is: many times following surgical placement of an A-V graft 10, it is found to have too much of a steal with its associated decreased perfusion to the hand and fingers. When this is detected, the annular balloon 230 can be inflated, as shown in FIGS. 3B and 6B, until a balance between the flow through the A-V graft 10 and to the hand and fingers is obtained. This may also be important if the patient has a change in cardiac output or blood pressure, changing the overall pressure and flow to the graft 10 and hand.

Figure 7:
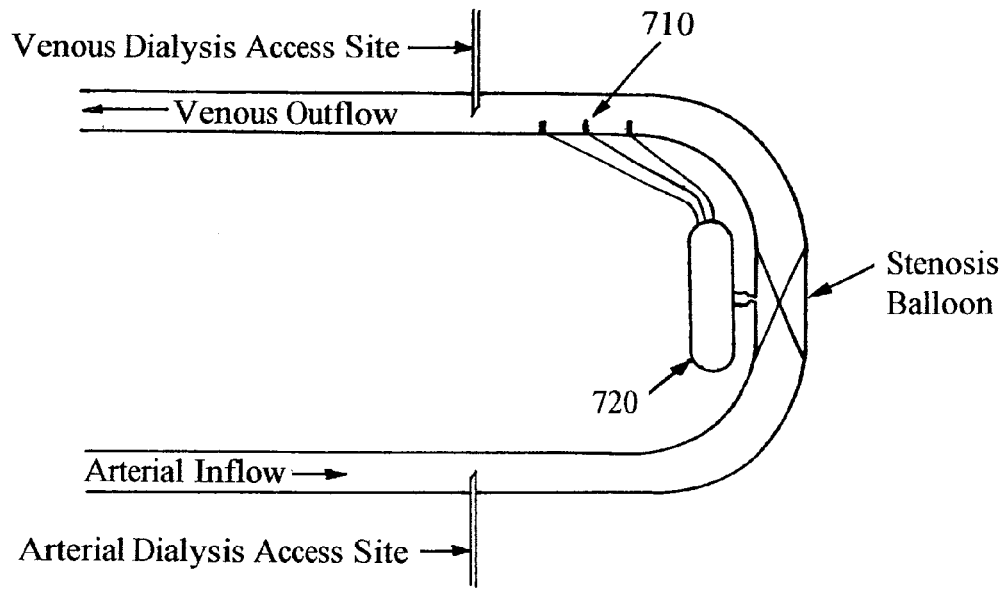
FIG. 7 is a side elevation view of the third embodiment with pressure and flow sensors at the venous end of the graft.

FIG. 7 shows a variation of the present invention where a series of pressure and flow sensors 710 are imbedded in the wall of the venous end of the dialysis graft. These are then connected to a monitor 720 that, when needed, will sense the venous environment and then adjust the balloon inflation level to optimize flow.

Figure 8:
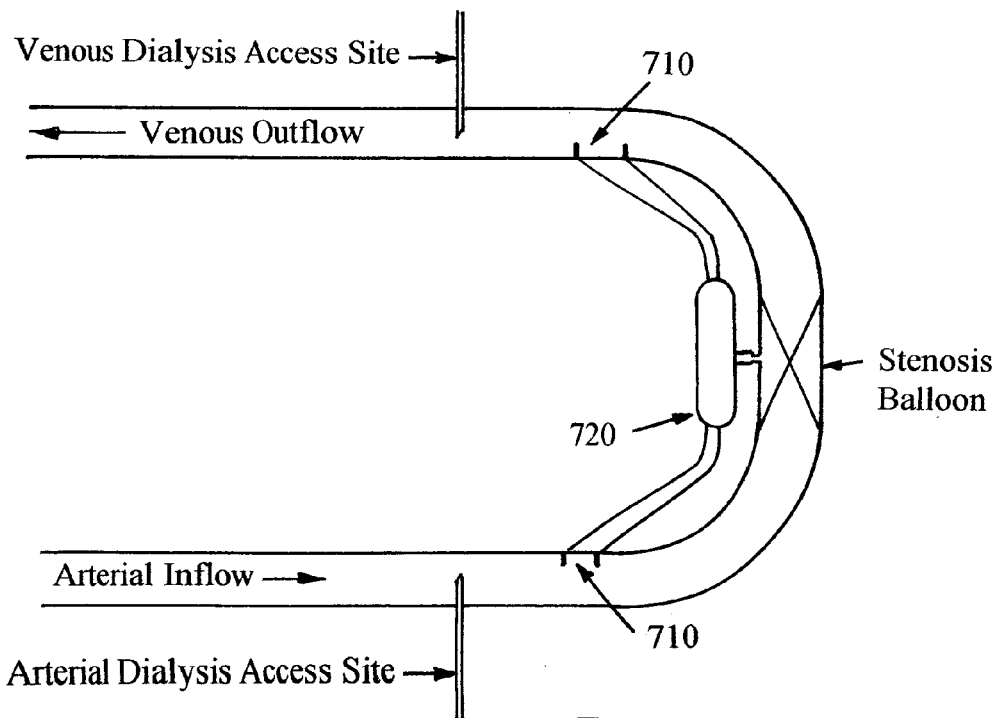
FIG. 8 is a side elevation view of the third embodiment with pressure and flow sensors at both the arterial and venous ends of the graft.

FIG. 8 shows another variation of the present invention wherein the A-V dialysis graft has flow and pressure sensors 710 at both the arterial and the venous limbs. The sensors 710 detect the variations in flow and then change the degree of stenosis optimizing flow.

FIGS. 9-11 show a variation of the present invention where a slit valve 810 is positioned between the arterial and venous ends of the dialysis graft.

FIGS. 12-15 show variations in the thin valves 820, 830, 840 and 850 suitable for creating a central stenosis.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

I claim:

1. An A-V dialysis graft having a streamwise direction and an upstream direction opposite the streamwise direction, the improved A-V dialysis graft construction comprising:
    an elongated length of tubing having a cross-sectional area, an inlet end and an outlet end, a direction from the inlet end to the outlet end comprising the streamwise direction;
    an inlet to a hemo-dialysis machine;
    a annular structure disposed within the tubing following said inlet to the hemo-dialysis machine in the streamwise direction, the annular structure having a constricted cross-sectional area less than the cross-sectional are of the tubing; and
    an outlet from the hemo-dialysis machine following, in the streamwise direction, the annular structure.

2. The graft of claim 1, wherein the annular structure is selectively movable between a contracted position and an expanded position, said annular structure providing a variable stenosis wherein said stenosis is less when the annular structure is contracted and greater when the annular structure is expanded.

3. The graft of claim 2, wherein the annular structure is an annular balloon selectively movable between a deflated mode and an inflated mode.

4. The graft of claim 2, further comprising:
    an environmental condition sensor disposed within the tubing following, in the streamwise direction, the annular structure; and
    a monitor electronically coupling the sensor and the movable annular structure, wherein the monitor selectively moves the annular structure based on conditions detected by the sensor.

5. The graft of claim 4, wherein a plurality of environmental sensors are disposed within the tubing following, in the streamwise direction, the annular structure.

6. The graft of claim 4, wherein the sensor detects environmental conditions selected from the group consisting of pressure, flow rate, pulsation, and turbulence.

7. The graft of claim 4, wherein a plurality of environmental sensors are disposed within the tubing both following and preceding, in the streamwise direction, the annular structure.

\* \* \* \* \*